United States Patent
Marash et al.

(10) Patent No.: US 7,796,730 B2
(45) Date of Patent: Sep. 14, 2010

(54) IRRADIATION TREATMENT APPARATUS AND METHOD

(75) Inventors: Michael Marash, Rishon Le'tzion (IL); Azriel Kadim, Elkana (IL)

(73) Assignee: P-Cure, Ltd., Or Yehuda (IL)

( * ) Notice: Subject to any disclaimer, the term of this patent is extended or adjusted under 35 U.S.C. 154(b) by 207 days.

(21) Appl. No.: 12/127,524

(22) Filed: May 27, 2008

(65) Prior Publication Data
US 2008/0292053 A1 Nov. 27, 2008

Related U.S. Application Data

(60) Provisional application No. 61/028,519, filed on Feb. 14, 2008, provisional application No. 60/939,923, filed on May 24, 2007.

(51) Int. Cl.
*A61N 5/10* (2006.01)
*G21K 5/08* (2006.01)
(52) U.S. Cl. .......................... 378/65; 378/68
(58) Field of Classification Search .......... 378/4, 378/20, 64, 65, 68, 195, 208
See application file for complete search history.

(56) References Cited

U.S. PATENT DOCUMENTS

| | | | |
|---|---|---|---|
| 2,145,686 A * | 1/1939 | Dessauer | 378/65 |
| 4,422,177 A * | 12/1983 | Mastronardi et al. | 378/17 |
| 4,618,133 A | 10/1986 | Siczek | |
| 4,870,287 A | 9/1989 | Cole et al. | |
| 5,013,018 A | 5/1991 | Sicek | |
| 5,036,530 A | 7/1991 | DiGiovanna et al. | |
| 5,039,867 A | 8/1991 | Nishihara et al. | |
| 5,247,556 A | 9/1993 | Eckert et al. | |

(Continued)

FOREIGN PATENT DOCUMENTS

DE 4103588 C1 5/1922

(Continued)

OTHER PUBLICATIONS

Kats, M. M., "Planar System Replacing Gantry for Protons and Carbon Ion Beams Transportation," Proceedings of the Sixth European Particle Accelerator Conference (EPAC '98), pp. 2362-2364, Moscow, Russia.

(Continued)

*Primary Examiner*—Irakli Kiknadze
(74) *Attorney, Agent, or Firm*—Simon Kahn

(57) ABSTRACT

The present disclosure provides an irradiation treatment apparatus having a generally vertical patient support surface; a patient securing mechanism arranged to secure a patient in a fixed relation to the patient support surface; a rotation platform secured at one end of the patient support surface and arranged to rotate the patient support surface about a generally vertical axis and optionally translate the patient support surface at least partially about a plane generally orthogonal to the generally vertical axis; an imager exhibiting a first mode in which the imager occludes radiation from a fixed beam irradiation source and a second mode in which the imager enables irradiation from the fixed beam irradiation source; and a vertical translation mechanism in communication with the patient support surface and arranged to translate the patient support surface along the generally vertical axis from a loading position to an irradiation position.

16 Claims, 14 Drawing Sheets

U.S. PATENT DOCUMENTS

| | | | |
|---|---|---|---|
| 5,250,019 | A | 10/1993 | McGinley |
| 5,398,356 | A | 3/1995 | Pfleger |
| 5,574,763 | A | 11/1996 | Dehner |
| 5,668,371 | A | 9/1997 | Deasy et al. |
| 5,740,224 | A * | 4/1998 | Muller et al. ............... 378/11 |
| 5,774,915 | A | 7/1998 | Scott et al. |
| 5,778,467 | A | 7/1998 | Scott et al. |
| 5,784,734 | A | 7/1998 | Scott et al. |
| 5,794,286 | A | 8/1998 | Scott et al. |
| 5,879,281 | A | 3/1999 | Ein-Gal |
| 5,983,424 | A | 11/1999 | Naslund |
| 6,094,760 | A | 8/2000 | Nonaka et al. |
| 6,148,058 | A * | 11/2000 | Dobbs ..................... 378/19 |
| 6,295,671 | B1 | 10/2001 | Reesby et al. |
| 6,375,355 | B1 | 4/2002 | Fortin |
| 6,386,759 | B2 | 5/2002 | Noettling |
| 6,400,791 | B1 | 6/2002 | Schwarz |
| 6,416,219 | B1 | 7/2002 | Pflaum et al. |
| 6,470,068 | B2 * | 10/2002 | Cheng ..................... 378/20 |
| 6,502,261 | B1 | 1/2003 | Harwood |
| 6,611,700 | B1 | 8/2003 | Vilsmeier et al. |
| 6,730,921 | B2 | 5/2004 | Kraft |
| 6,742,929 | B2 | 6/2004 | Horbaschek |
| 6,769,806 | B2 | 8/2004 | Moyers |
| 6,780,149 | B1 | 8/2004 | Schulte |
| 6,785,360 | B1 | 8/2004 | Annis |
| 6,802,564 | B2 | 10/2004 | Brockway et al. |
| 6,814,694 | B1 | 11/2004 | Pedroni |
| 6,828,792 | B1 | 12/2004 | Danby et al. |
| 6,865,253 | B2 | 3/2005 | Blumhofer et al. |
| 6,865,411 | B2 | 3/2005 | Erbel et al. |
| 6,894,300 | B2 | 5/2005 | Reimoser et al. |
| 6,986,179 | B2 | 1/2006 | Varadharajulu et al. |
| 7,000,271 | B2 | 2/2006 | Varadharajulu |
| 7,003,070 | B1 | 2/2006 | Chen et al. |
| 7,020,232 | B2 | 3/2006 | Rand et al. |
| 7,043,784 | B2 | 5/2006 | Plannerer |
| 7,062,007 | B2 | 6/2006 | Morita |
| 7,077,569 | B1 | 7/2006 | Tybinkowski et al. |
| 7,125,167 | B2 | 10/2006 | Alakkat |
| 7,137,160 | B2 | 11/2006 | Hand et al. |
| 7,154,991 | B2 | 12/2006 | Earnst et al. |
| 7,173,265 | B2 | 2/2007 | Miller et al. |
| 7,640,607 | B2 | 1/2010 | Guertin et al. |
| 2002/0057758 | A1 | 5/2002 | Stark |
| 2002/0095722 | A1 | 7/2002 | Korver, II et al. |
| 2002/0120986 | A1 | 9/2002 | Erbel et al. |
| 2003/0058993 | A1 | 3/2003 | Bohn |
| 2003/0072416 | A1 | 4/2003 | Rasche et al. |
| 2003/0078523 | A1 | 4/2003 | Burkhardt et al. |
| 2003/0164459 | A1 | 9/2003 | Schardt et al. |
| 2004/0013239 | A1 | 1/2004 | Gregerson et al. |
| 2004/0042583 | A1 | 3/2004 | Wackerle et al. |
| 2004/0102698 | A1 | 5/2004 | Vilsmeier et al. |
| 2004/0125920 | A1 | 7/2004 | Zaiki |
| 2004/0162457 | A1 | 8/2004 | Maggiore et al. |
| 2004/0172758 | A1 | 9/2004 | Alakkat |
| 2004/0199072 | A1 | 10/2004 | Sprouse et al. |
| 2005/0065675 | A1 | 3/2005 | Georgi et al. |
| 2005/0138732 | A1 | 6/2005 | Erbel et al. |
| 2005/0222505 | A1 | 10/2005 | Damadian et al. |
| 2005/0228255 | A1 | 10/2005 | Saracen et al. |
| 2005/0281374 | A1 | 12/2005 | Cheng et al. |
| 2006/0002511 | A1 | 1/2006 | Miller et al. |
| 2006/0042009 | A1 | 3/2006 | Somasundaram et al. |
| 2006/0050848 | A1 | 3/2006 | Vilsmeier et al. |
| 2006/0106301 | A1 | 5/2006 | Kats |
| 2006/0262898 | A1 | 11/2006 | Partain et al. |
| 2007/0003010 | A1 | 1/2007 | Guertin et al. |
| 2008/0086816 | A1 | 4/2008 | Farooqui |
| 2009/0168960 | A1 | 7/2009 | Jongen et al. |

FOREIGN PATENT DOCUMENTS

| | | |
|---|---|---|
| EP | 1121957 A2 | 8/2001 |
| EP | 1380262 A1 | 1/2004 |
| EP | 1384494 A1 | 1/2004 |
| EP | 1288322 A1 | 2/2004 |
| EP | 1388322 A1 | 2/2004 |
| EP | 1454653 A1 | 9/2004 |
| EP | 1867284 A1 | 12/2007 |
| JP | 03-075071 A2 | 3/1991 |
| JP | 08-229145 A2 | 9/1996 |
| JP | 2001-095932 A2 | 4/2001 |
| JP | 2001161839 A | 6/2001 |
| WO | WO 94/10908 A3 | 5/1994 |
| WO | WO 98/18523 A1 | 5/1998 |
| WO | WO 99/53997 A1 | 10/1999 |
| WO | WO 03/059433 A2 | 7/2003 |
| WO | WO 03/070101 A1 | 8/2003 |
| WO | WO 2004/010381 A1 | 1/2004 |
| WO | WO 2005/018734 A2 | 3/2005 |
| WO | 2007/012649 A1 | 2/2007 |
| WO | 2007/017211 A2 | 2/2007 |
| WO | WO 2007/012649 A1 | 2/2007 |
| WO | WO 2007/017211 A2 | 2/2007 |
| WO | 2007/045076 A1 | 4/2007 |
| WO | WO 2007/045076 A1 | 4/2007 |
| WO | WO 2007/062788 A1 | 6/2007 |

OTHER PUBLICATIONS

Kamada, Tadashi et al., "A Horizontal CT System Dedicated to Heavy-Ion Beam Treatment," Radiotherapy & Oncology 50 (1999), pp. 235-237, Elsevier Science Ireland Ltd., Shannon, Ireland.

Office Action for U.S. Appl. No. 12/127,391 Mail Date Mar. 24, 2010.

International Search Report for Parallel PCT Application PCT/IL2008/000699 issued Oct. 6, 2008, European Patent Office.

Written Opinion of the International Searching Authority for Parallel PCT Application PCT/IL2008/000699 issued Oct. 6, 2008, European Patent Office, mailed Oct. 24, 2008.

* cited by examiner

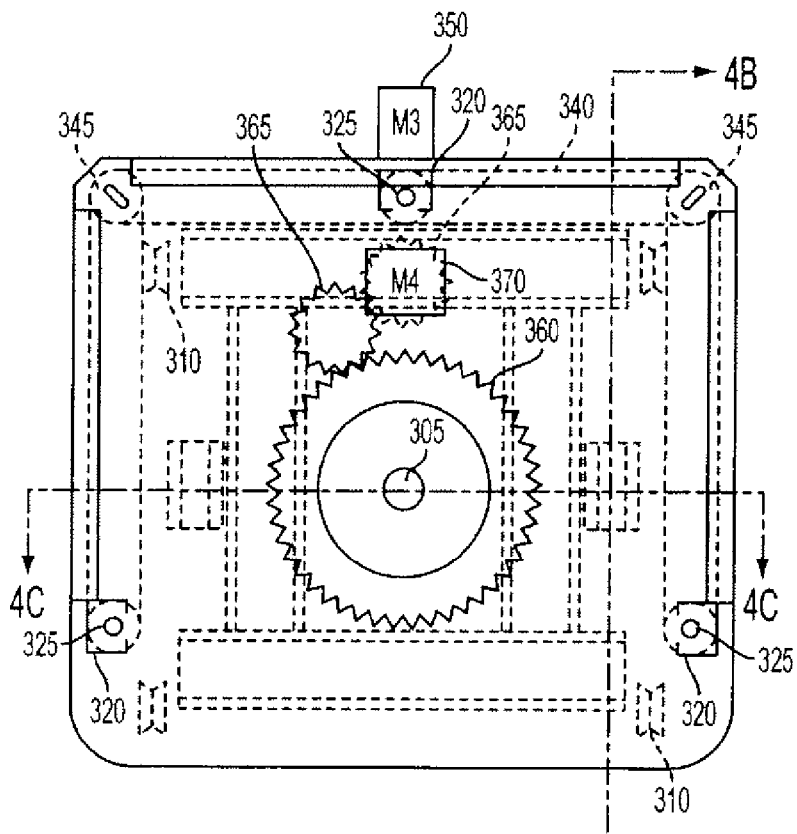
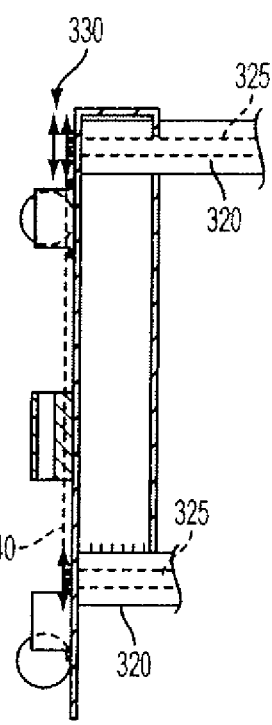
FIG. 4A  FIG. 4B
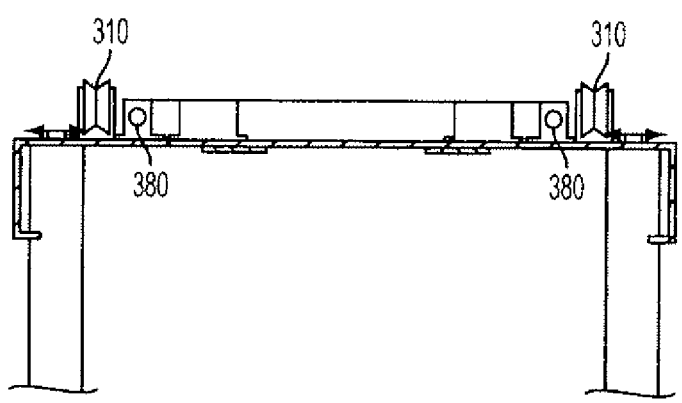
FIG. 4C

IRRADIATION TREATMENT APPARATUS AND METHOD

CROSS-REFERENCE TO RELATED APPLICATIONS

This application claims priority from U.S. Provisional Patent Application Ser. No. 60/939,923 filed May 24, 2007, entitled "Teletherapy Positioning and Validation," and U.S. Provisional Patent Application Ser. No. 61/028,519, bearing the present title, filed Feb. 14, 2008. This application is also related to U.S. patent application Ser. No. 12/127,391, entitled "Method and Apparatus for Teletherapy Positioning and Validation," filed on May 27, 2008. Each of the above applications is incorporated herein by reference.

TECHNICAL FIELD

The present disclosure relates generally to the field of teletherapy and in particular to a system and method for positioning and validation of a patient before a fixed beam irradiation source.

BACKGROUND

Teletherapy generally employs an irradiation source disposed at a distance from the body to be treated. X-rays and electron beams have been used in teletherapy to treat various cancers. However, X-rays and electron beams exhibit an energy transfer characteristic approaching an exponential attenuation function and are therefore not optimal for treating deeply embedded growths or target areas. Recently, the use of heavy particles particularly hadrons, in teletherapy has found increasing acceptance, in part because of the ability of heavy particles to penetrate to a specific depth without appreciably harming intervening tissue. In particular, the energy transfer characteristic of hadrons exhibits an inversed depth profile with a Bragg peak at a location where the hadrons deposit most of their energy, which is approximately at the end of the hadrons' path. As a result of this hadron energy transfer characteristic, increased energy can be directed at or deposited in an embedded growth as compared to X-rays and electron beams. Also, less damage to healthy intervening tissue results when hadron beams are used to treat deep-seated tumors or diseased target tissue.

It should be appreciated that the term "hadrons" can refer to a variety of particles, including protons and other ions that are used in therapy. While this document describes treatment as being accomplished with protons, this is not meant to be limiting in any way and other types of hadrons and ions can be included in such discussion where appropriate.

Typically, in a therapy system, the charged protons or ions are focused into narrow, intensity-modulated, scanned pencil beams of variable penetration depth. In this way, the dose profile can be matched to the target volume. In order to ensure complete irradiation of the target growth, a plurality of beams arriving at the embedded growth from several different directions can be used. The volume in which the plurality of beams intersects, whether the beams are provided sequentially or simultaneously, is often referred to as an isocenter. To improve the biological effectiveness of the treatment, the isocenter is collocated with the target growth to deliver the maximum treatment dose to the target volume and to spare the surrounding tissue.

Present teletherapy systems use a gantry apparatus carrying a beam generating and delivery system. The gantry is a motorized or powered apparatus for moving the massive particle delivery system around a patient who is typically immobilized on a treatment table. Since the beam generating and delivery system is large and extremely heavy, such gantry systems are prohibitively expensive, limiting the number of available proton therapy centers that can provide services to patients. Furthermore, the spatial range of such gantry-driven systems is limited due to mechanical constraints. Movement of the beam generating and delivery system from location to location in order to effect the delivery of the plurality of beams leads to an offset in the isocenter which must be carefully adjusted prior to beam delivery. One example of the above-described treatment systems is illustrated in U.S. Pat. No. 6,769,806 to Moyers.

For example, World Intellectual Property Organization Publication WO 2007/012649 published Feb. 1, 2007 to Siemens Aktiengescllshaft, is directed to a device for obtaining image data for planning a radiation therapy, comprising a computerized tomography (CT) gantry and a patient positioning unit. The CT gantry is arranged in a moveable fashion in such a way that imaging for the purposes of radiation therapy can be carried out in this body position of the patient. The need for a freely moveable CT gantry adds to cost, as a CT of the quality necessary for preferred imaging can weigh 2 metric tons or more.

Imagers have been available for use in the context of patient treatment, for example as appear in U.S. Pat. No. 6,949,941 issued Sep. 6, 2005 to Gregerson et al., entitled "Breakable Gantry Apparatus for Multidimensional X-ray Based Imaging."

Additionally, the prior art requires separate arrangements for treatment planning and irradiation. Such a need for a plurality of arrangements further adds to the cost of the system and diminishes its practical availability.

There is thus a need for an improved teletherapy apparatus that overcomes some or all of the above limitations.

SUMMARY

In view of the discussion provided above and other considerations, the present disclosure provides methods and apparatus to overcome some or all of the disadvantages of prior and present teletherapy systems and methods. Other new and useful advantages of the present methods and apparatus will also be described herein and can be appreciated by those skilled in the art.

In one embodiment, this is provided by an irradiation treatment apparatus comprising a patient securing means arranged to secure a patient in a generally vertical position to a patient support surface. The patient support surface is connected at one end to a rotatable platform, arranged to rotate the patient support surface about a generally vertical axis thereof and to optionally translate the patient support surface along at least a portion of a plane perpendicular to the axis of rotation. The patient support surface is further translatable vertically, generally along the axis of rotation and arranged generally before a fixed beam irradiation source.

In one embodiment, an imager, preferably a computerized tomography (CT) imager, exhibiting two modes of operation is provided. In a first mode, the imager occludes the fixed beam irradiation source, and in a second mode the imager enables irradiation from the fixed beam irradiation source.

In one particular embodiment, the imager is translatable vertically between the first and second modes. In another particular embodiment the imager exhibits a radially shiftable section, with the first mode representative of the imager being a substantially closed ring and the second mode representative of the imager with section radially shifted.

In yet another particular embodiment the imager is provided with a window for passage of the treatment irradiation beam with the first mode representative of the window being closed and the second mode representative of the window being open.

Preferably, the imager in the first mode provides fine resolution images sufficient for treatment planning. In certain embodiments the second mode provides sufficient definition for inter-treatment verification and intra-treatment verification.

In one embodiment the patient is loaded onto the patient support surface, platform, or generally, member, in a loading position, and the patient support member is translated vertically to approximately align a target tissue with a fixed beam irradiation source. The patient support surface is further translated horizontally and/or rotated so as to approximately align the target tissue with the ultimate path of a fixed beam of irradiation at the desired angle to treat a target volume of diseased tissue.

It is to be understood that the term fixed beam irradiation source, as used in this document, does not exclude scanning and scattering technologies, which are sourced from a fixed location charged hadron source with post beam generation scanning or scattering functionality. It is also to be understood that the term fixed beam irradiation source, as used in this document, is not limited to a single fixed beam irradiation source, and multiple fixed beams, which are independently controlled or joint controlled, may be supplied without exceeding the scope of the invention.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which numerals designate corresponding elements or sections throughout.

FIG. 4A illustrates an exemplary, partially cut away, top view of a base support for the patient platform of FIG. 1, including a mechanism for translating an imager and a mechanism for rotating a patient support surface;

FIG. 4B illustrates an exemplary cut 4B of the base support of FIG. 4A;

FIG. 4C illustrates an exemplary cut 4C of the base support of FIG. 4A;

DETAILED DESCRIPTION

Figure 1:
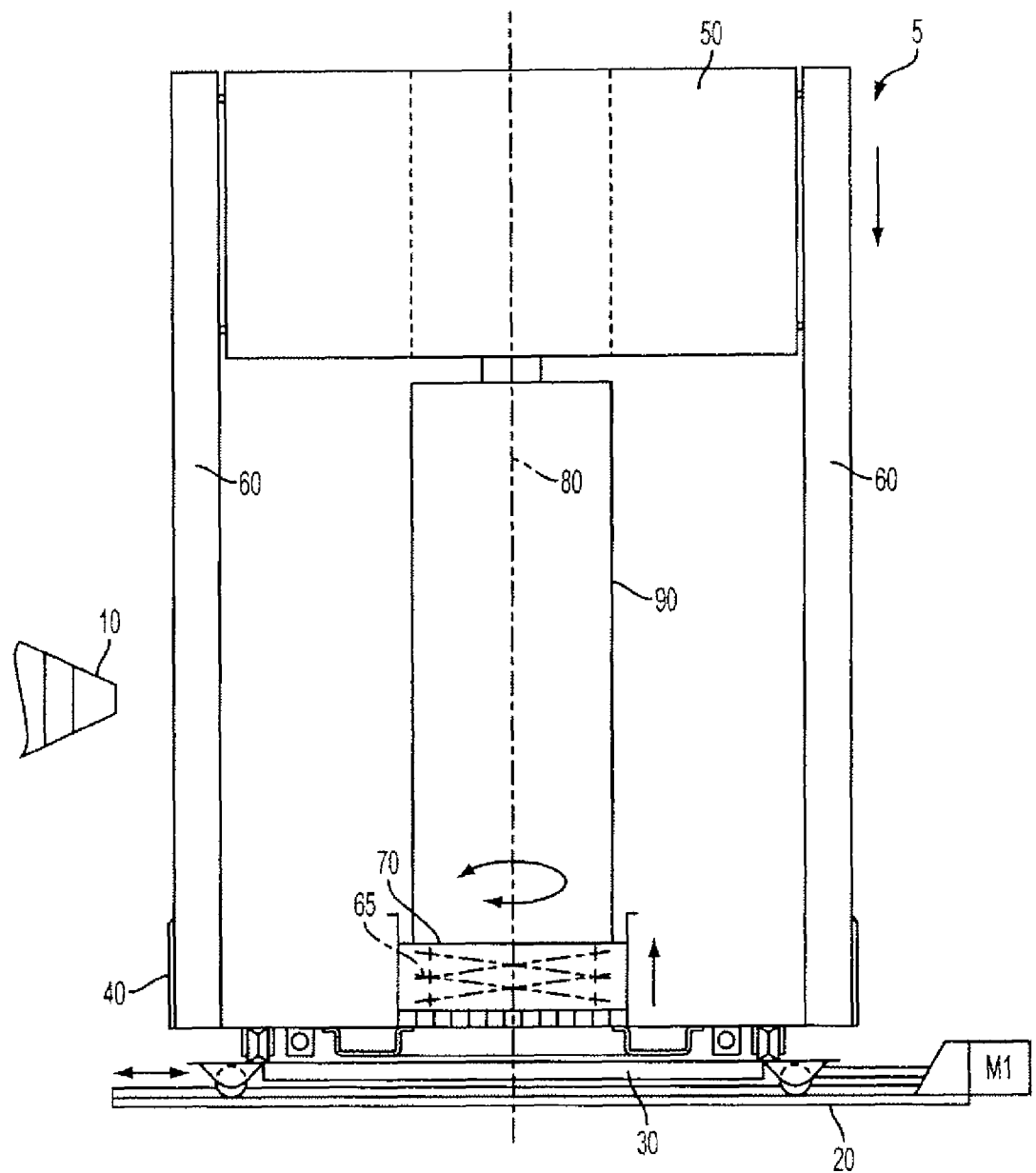
FIG. 1 illustrates an exemplary embodiment of an irradiation treatment apparatus and treatment.

Some or all of the present embodiments provide and enable an irradiation treatment apparatus which preferably further provides treatment planning.

Where a patient is referred to, the patient is preferably a live human, but can also be an animal, other suitable organs, or target for application of the present teletherapy thereto.

The target tissue is delineated from adjacent non-target tissue; a planned target volume (PTV) is determined; and a plurality of beam angles and the preferred distance of the delineated target tissue from the treatment irradiation beam source for each of the plurality of angles is determined.

It is also to be understood that fixed beam irradiation may include scanning and scattering technologies, which are sourced from a fixed location charged hadron source with post beam generation scanning or scattering functionality. In addition, fixed beam irradiation is not limited to that from a single fixed beam irradiation source, but can include multiple fixed beams which are independently controlled or jointly controlled.

In one embodiment, the irradiation treatment apparatus comprises a patient securing means arranged to secure a patient in a generally vertical position to a patient support surface. The patient support surface is connected at one end to a rotatable and translatable platform, arranged to rotate the patient support surface about a generally vertical axis thereof and to translate the patient support surface along a plane perpendicular to the axis of rotation. The patient support surface is further translatable vertically, generally along the axis of rotation. An imager, preferably a computerized tomography imager exhibiting fine resolution, is provided and arranged to be translatable vertically. In one further embodiment, the imager is translatable between a first neutral position and a second imaging position. In another embodiment the imager is translatable over a range of positions. In yet another embodiment the imager is fixed, and is arranged to change from a mode in which the treatment irradiation beam is occluded from the patient and a mode in which the treatment irradiation beam is arranged to impact the patient.

The patient is loaded onto the patient support surface in a loading position, and the patient support surface it translated vertically to approximately align a target tissue with a fixed beam irradiation source. The patient support surface is further rotated, and optionally translated horizontally, so as to approximately align the target tissue with the ultimate beam of irradiation at the desired angle.

Optionally, and advantageously, the irradiation treatment apparatus can in one embodiment be further utilized for treatment planning, particularly in an embodiment in which the imager is of sufficiently fine resolution.

In the event that multiple treatment angles are prescribed the above is repeated for each treatment angle, preferably with imaging after each translation or rotation of the patient support surface.

In order to accomplish teletherapy in accordance with an embodiment of the subject invention, a fixed beam irradiation source is supplied in a treatment room. In one embodiment the fixed beam irradiation source is arranged to controllably output a generally horizontal beam, and in another embodiment the fixed beam irradiation source is arranged to controllably output a generally angled beam up to 45° from horizontal. It is understood that unless specifically limited by the particular instance, where angles and orientations are referred to herein, such are only provided by way of example, and other angles or orientations can be included within the scope of the present discussion.

In yet another embodiment multiple fixed beams, which are independently controlled or joint controlled, may be supplied without exceeding the scope of the invention. The fixed beam irradiation source may further exhibit post scanning or scattering functionality without exceeding the scope of the invention. Preferably, the fixed beam irradiation source exhibits an exit nozzle, which may be telescoped or otherwise translated to a prescribed distance from the target tissue.

As stated earlier and elsewhere it is to be appreciated that the invention is not limited in its application to the details of construction and the arrangement of the components set forth in the following description or illustrated in the drawings. The invention also comprehends other embodiments and can be practiced or carried out in various ways.

FIG. 1 illustrates an exemplary high level frontal view of a first embodiment of an irradiation treatment apparatus and treatment arrangement. The apparatus includes a fixed beam irradiation source 10 and an irradiation treatment apparatus 5 and a control unit 15. Irradiation treatment apparatus 5 includes a first base rail platform 20, a translatable second base rail platform 30, a translatable platform 40 and an imager 50. Translatable platform 40 comprises: a base support 55, an imager vertical translation mechanism 60, a platform vertical translation mechanism 65, a patient platform 70 and a patient support surface or member 90. Patient platform 70 is rotatable around an axis 80 and is vertically translatable by vertical translation mechanism 65 in relation to base support 55. Patient support surface 90 is arranged to secure a patient in a generally vertical position, and is secured at one end to patient platform 70. Imager 50 is vertically translatable by imager vertical translation mechanism 60. The translation mechanisms of translatable second base rail platform 30, translatable platform 40 and patient support surface 70 will be described further in relation to FIGS. 2, 3 and 5, respectively. Platform vertical translation mechanism 60 will be described further relation to FIG. 4.

Imager 50 is illustrated as a circular CT imager, however this is not meant to be limiting in any way. In another embodiment imager 50 is selected from among an ultrasound imager, a CT imager, a magnet resonance imager, an x-ray imager, a fluoroscope, a positron emission tomography imager and a single photon emission computed tomography imager, and may comprise a combination of imagers without exceeding the scope of the invention.

In operation, patient platform 70 is placed in a loading position by platform vertical translation mechanism 65, and the patient is loaded and secured to patient support surface 90. Patient platform 70 is then translated by platform vertical translation mechanism 65, in relation to base support 55, to approximately align a target tissue with fixed beam irradiation source 10. Patient platform 70 is further translated horizontally, if required, by translatable second base rail platform 30 and translatable platform 40, and rotated around axis 80 so as to approximately align the target tissue of the patient secured to patient support surface 90 with the ultimate beam of irradiation exiting fixed beam irradiation source 10 at the desired angle.

Imager 50 is translated vertically to the imaging position by imager vertical translation mechanism 60, and the target tissue is imaged. Again it is pointed out that when referring to vertical direction or orientation, it is intended to include substantially vertical direction or orientation. The same generalization applies to discussion of horizontal or other, directions and orientations.

In the imaging position, imager 50 occludes the ultimate beam from fixed beam irradiation source 10. Responsive to the image, fine tuning of the vertical translation, rotation and horizontal translation of patient platform 70, if required, is performed. Imager 50 is then translated vertically by imager vertical translation mechanism 60 to a neutral position in which imager 50 does not occlude the ultimate beam from fixed beam irradiation source 10. Optionally, a nozzle or aperture of fixed beam irradiation source 10 is translated generally along the ultimate irradiation beam axis, so that the nozzle or aperture is at a predetermined distance from the target tissue, and irradiation from the fixed beam irradiation source is performed without further movement of the patient.

In the event that multiple treatment angles are prescribed the above is optionally repeated for each treatment angle, further optionally with imaging after each rotation, or optional translation, of patient platform 70.

Irradiation treatment apparatus 5 is being described in an embodiment in which patient platform 70 may be translated along a plane, however this is not meant to be limiting in any way. In another embodiment, patient platform 70 is only partially translatable about a plane, with the balance of the translation effective supplied by the articulation of fixed beam irradiation source 10 along the axis of irradiation.

In a preferred embodiment imager 50 and all translation and rotation mechanisms are responsive to control unit 15.

Figures 2A, 2B:
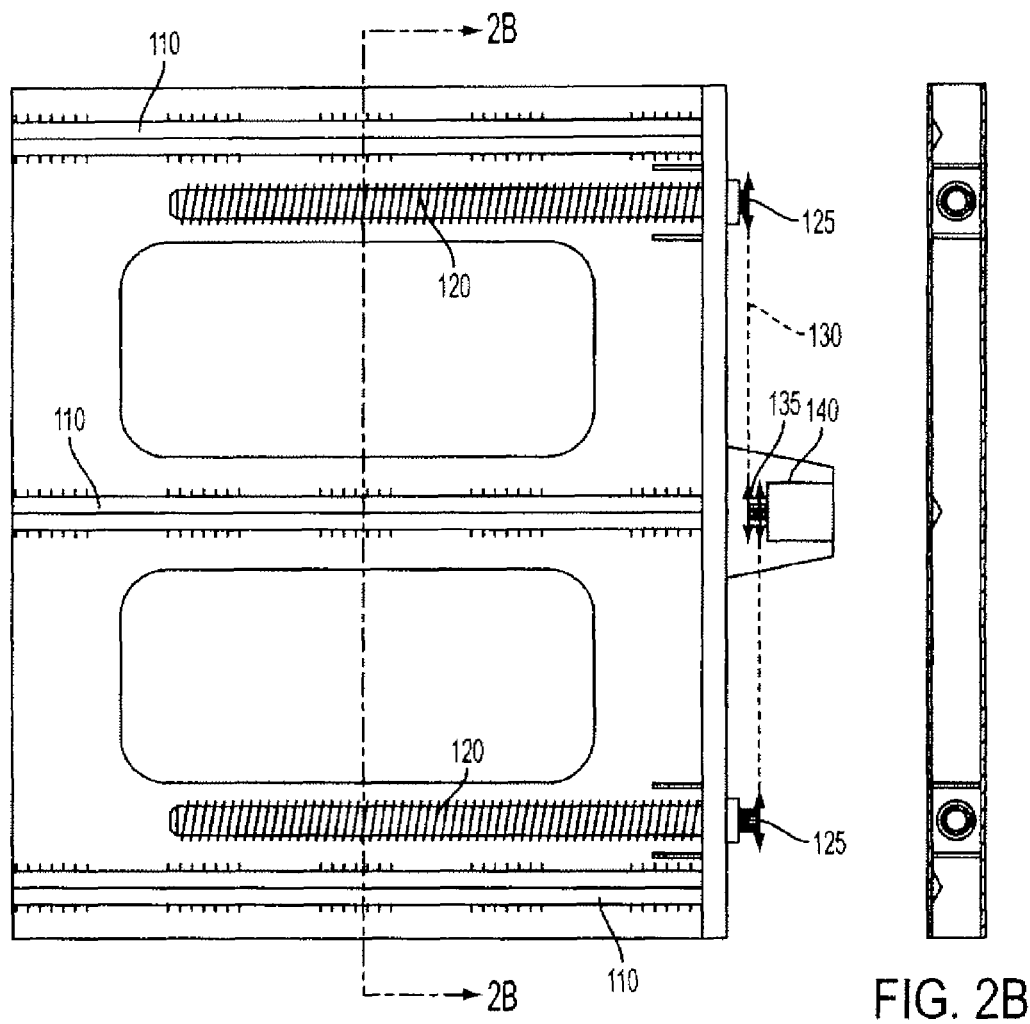
FIG. 2A illustrates en exemplary embodiment of a first base rail platform of the irradiation treatment apparatus of FIG. 1.
FIG. 2B illustrates an exemplary cut 2B of the first base rail platform of FIG. 2A.

FIG. 2A illustrates an exemplary high level top view of first base rail platform 20 of the irradiation treatment apparatus 5 of FIG. 1, including a plurality of rails 110, a plurality of extended screws 120, a tooth gear 125, a pair of chains 130, a tooth gear 135 and a motor 140. Motor 140 is arranged to move chains 130 horizontally by engaging with tooth gear 135 connected to the shaft of motor 140. Each of extended screws 120 are arranged to engage a respective chain 130 by the respective tooth gear 125 arranged at an end of the respective extended screw 120. FIG. 2B illustrates cut 2B of first base rail platform 20 of FIG. 2A.

In operation, motor 140 turns tooth gear 135 which interacts with chains 130, thereby moving chains 130. Chains 130 interact with a respective tooth gear 125, thereby turning the respective extended screw 120. Extended screws 120 represent the translation mechanism of translatable second base rail platform 30, as will be described further in FIG. 3B.

Figure 3A:
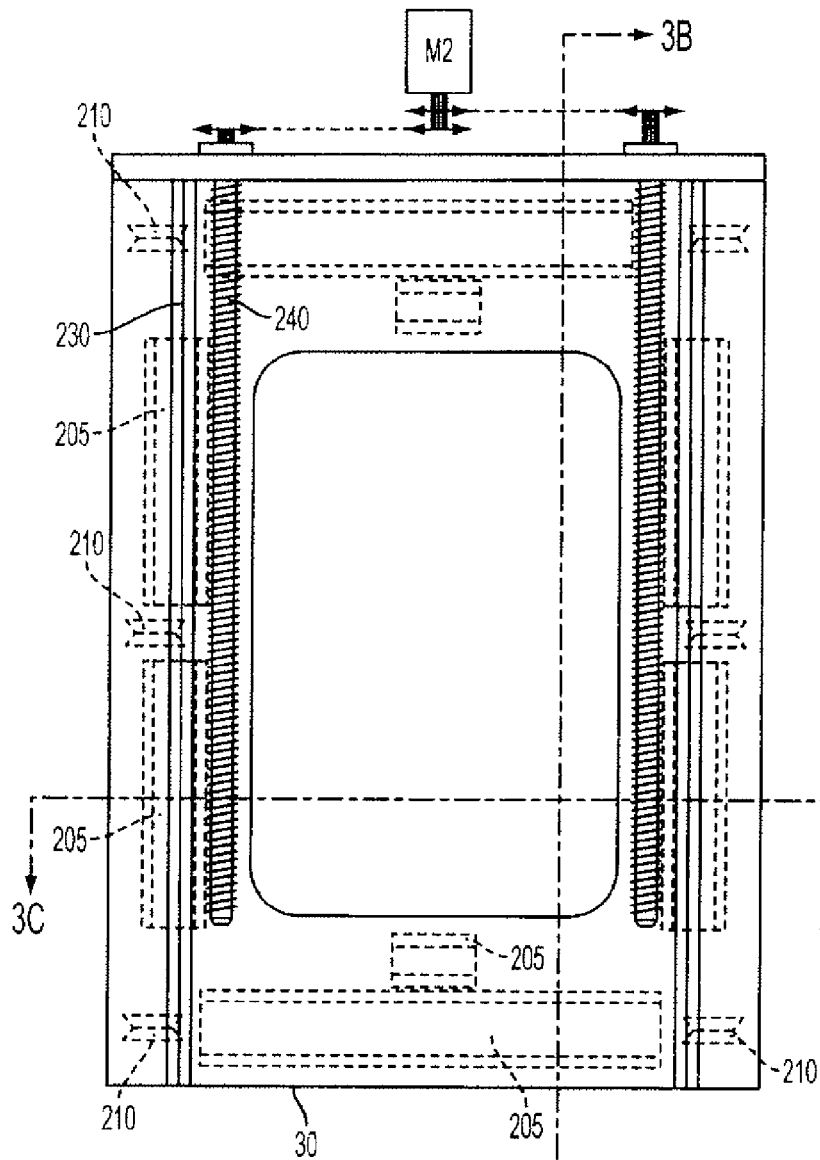
FIG. 3A illustrates an exemplary embodiment of a translatable second base rail platform of the irradiation treatment apparatus of FIG. 1.

FIG. 3A illustrates an exemplary high level top view drawing of translatable second base rail platform 30 of irradiation treatment apparatus 5 of FIG. 1, including a plurality of strengthening members 205, a plurality of wheels 210, a plurality of rails 230, a plurality of extended screws 240 each exhibiting a tooth gear 245, a pair of chains 250, and a motor 260 exhibiting a tooth gear 255 connected to the shaft thereof. Tooth gear 255 and tooth gears 245 each engage chain 250 at respective locations.

In operation, motor 260 turns tooth gears 255 which interacts with chain 250, thereby moving chain 250. Moving chain 250 interacts with each tooth gear 245, thereby turning extended screws 240. Extended screws 240 represent the translation mechanism of translatable platform 40, as will be described further in relation to FIG. 3C. Wheels 210 run along rails 110 of first base rail platform 20 of FIG. 2.

Figure 3B:
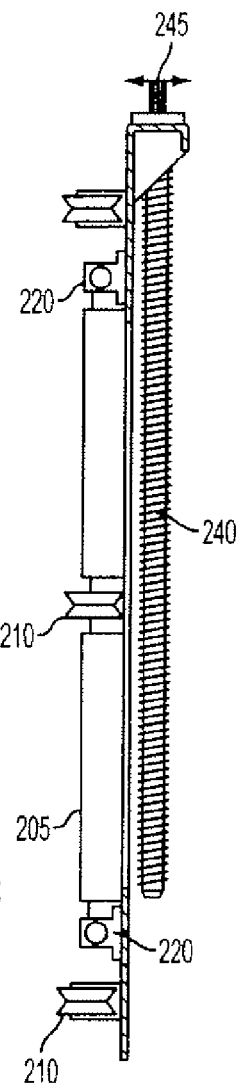
FIG. 3B illustrates en exemplary cut 313 of the translatable second base rail platform of FIG. 3A.

FIG. 3B illustrates an exemplary cut 313 of translatable second base rail platform 30 of FIG. 3A. Extended screws 120 of FIG. 2 are placed through a respective nut 220. In operation, extended screws 120 are rotated as described above in relation to FIG. 2, thereby translating translatable second base rail platform 30 along rails 110 of first base rail platform 20 of FIG. 2, with wheels 210 engaging rails 110.

Figure 3C:
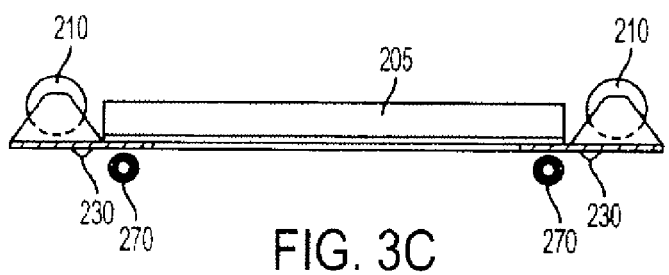
FIG. 3C illustrates an exemplary cut 3C of the translatable second base rail platform of FIG. 3A.

FIG. 3C illustrates an exemplary cut 3C of translatable second base rail platform 30 of FIG. 3A. Residing on rails 230 are wheels 210 of translatable platform 40 of FIG. 1, as will be described further in FIGS. 4A, 4B. Extended screws 240 of FIG. 3A are placed through a respective nut 270 of platform 40, as will be further in FIGS. 4A, 4B. In operation, extended screws 240 are rotated as described above, thereby translating translatable platform 40 of FIG. 1 along the rails of second base rail platform 200 of FIG. 3A, with wheels of translatable platform 40 running along rails 230.

In some embodiments, the longitudinal axis of rails 230 are arranged to be orthogonal to the longitudinal axis of rails 110 thereby enabling translation of patient platform 70 about a horizontal plane.

Figure 5A:
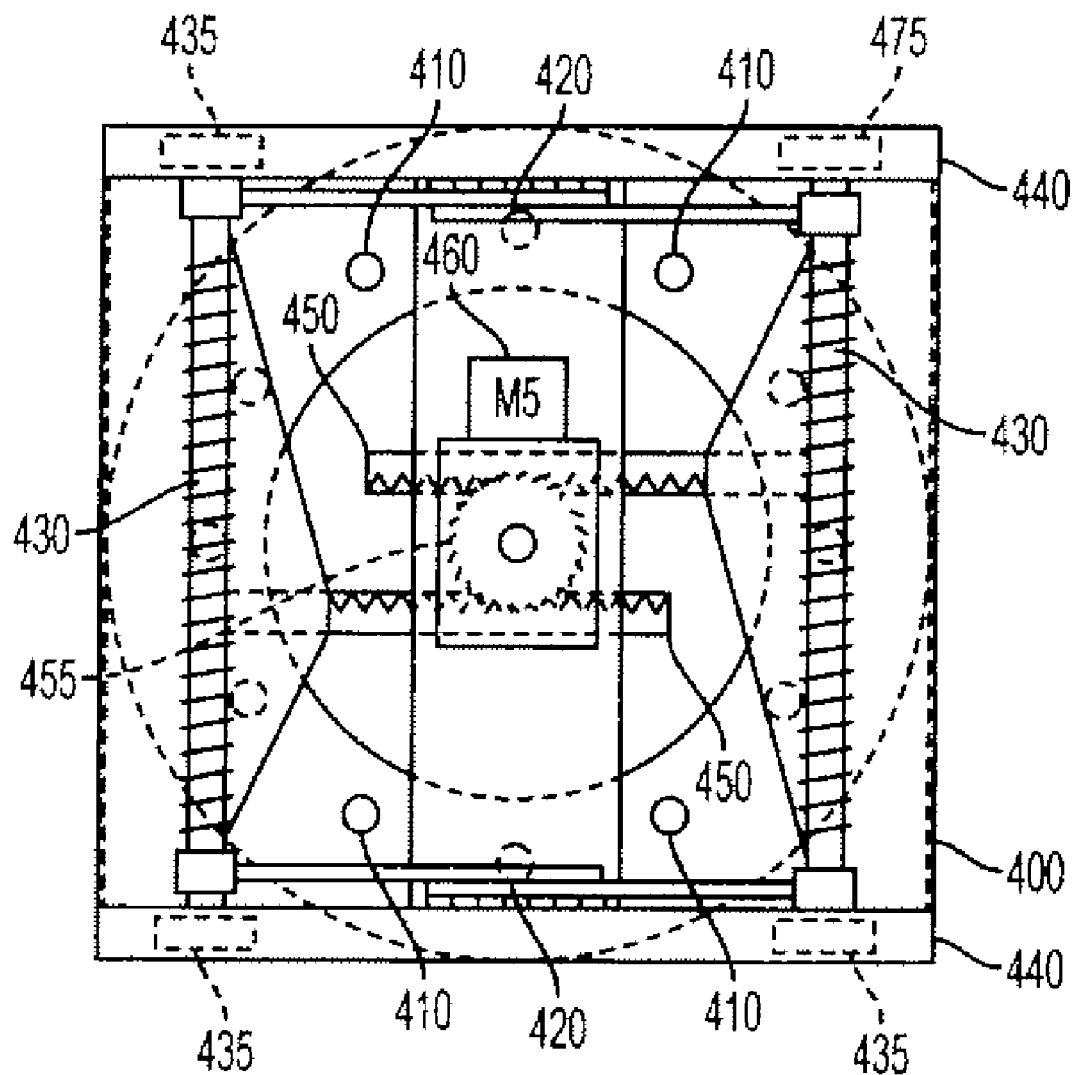
FIG. 5A illustrates an exemplary, partially cut away, top view of a patient platform including a scissor mechanism in the closed position for translating the patient platform vertically.

FIG. 4A illustrates an exemplary high level, partially cut away, top view of base support 55 of irradiation treatment apparatus 5 of FIG. 1, including a hole 305, a plurality of wheels 310, a plurality of channels 320 each enclosing a respective extended screw 325, a chain 340; a plurality of pulleys 345, a motor 350, a strengthening ring 360, a plurality of tooth gears 365 and a motor 370. A centering pin of a base for patient support surface 70 of FIG. 1, as will be described further in FIG. 5A, is placed in hole 305. Wheels 310 run along rails 230 of translatable second base rail platform 30 of FIG. 3A, as described above in relation to FIG. 3C. Extended screws 325 of respective channels 320 each exhibit a tooth gear 330, as will be described further in relation to FIG. 4B, which are arranged to engage chain 340. Chain 340 is arranged to run substantially around the perimeter of base support 55 by pulleys 345, and engages a tooth gear (not shown) connected to the shaft of motor 350.

In operation, motor 350 interacts with chain 340 thereby moving chain 340, and moving chain 340 interacts with tooth gears 330 connected to extended screws 325, as described further in relation to FIG. 4B, thereby turning extended screws 325. Extended screws 325 interact with one of fixed slots on imager 50 (not shown), or nuts attached thereto, thereby translating imager 50 vertically.

Motor 370, which exhibits a tooth gear 365 attached to the shaft thereof, turns a large tooth gear 470, which will be explained further in relation to FIG. 5A, by meshing through an intermediary tooth gear 365. Patient platform 70 of FIG. 1 is connected to large tooth gear 360, as will be described further in relation to FIG. 5A. Thus, in operation motor 370 rotates patient platform 70 by turning large tooth gear 360.

FIG. 4B illustrates an exemplary cut 413 of base support 55 showing tooth gears 330 of extended screws 325 and FIG. 4C illustrates cut 4C of base support 55. Extended screws 240 of FIG. 3A are arranged to pass through a respective nut 380. In operation, as described above in relation to FIG. 3C, extended screws 240 are rotated as described in FIG. 3A, thereby translating platform base 55 along the rails of second base rail platform 30 of FIG. 3A, with wheels 310 running along rails 230 of second base rail platform 30.

FIG. 5A illustrates an exemplary high level, partially cut away, top view of patient platform 70, including a scissor mechanism in the closed position, for translating patient platform 70 vertically. In some embodiments, patient platform 70 includes a plurality of connecting members 410, a scissor mechanism 420, a pair of beams 430, a plurality of runners 435, a pair of channels 440, a pair of toothed linear members 450, a tooth gear 455, a motor 460 and a large tooth gear 470. Connecting members 410 are arranged to connect patient platform 70 to large tooth gear 360 of base support 55 of FIG. 4A and a centering pin 490 of base 400 (shown in FIG. 5B) is placed in hole 305 of base support 55, thereby enabling rotation of patient platform 70 of FIG. 1 when large tooth gear 470 is turned as described above in relation to FIG. 4A. Scissor mechanism 420 is connected at and thereof to beams 430, beams 430 being connected at their ends to runners 435, which are placed in channels 440. Each beam 430 is also connected to a toothed linear member 450. Toothed linear members 450 are arranged to mesh with tooth gear 455. Motor 460 exhibits a tooth gear (not shown) arranged to mesh with a tooth gear on the shaft of tooth gear 455. Tooth gear 455 is arranged to mesh with toothed linear member 450.

In operation, motor 460 rotates tooth gear 455 which translates toothed linear members 450 in unison. As toothed linear members 450 are translated, beams 430 are also translated, thereby opening or closing scissor mechanisms 420. Opening scissor mechanisms 420 causes patient platform 70 of FIG. 1 to translate vertically towards imager 504 closing scissor mechanisms 420 causes patient platform 70 to translate vertically towards imager 50 translatable platform 40. Runners 435 are arranged inside channels 440 to keep beams 430 straight.

Figure 5B:
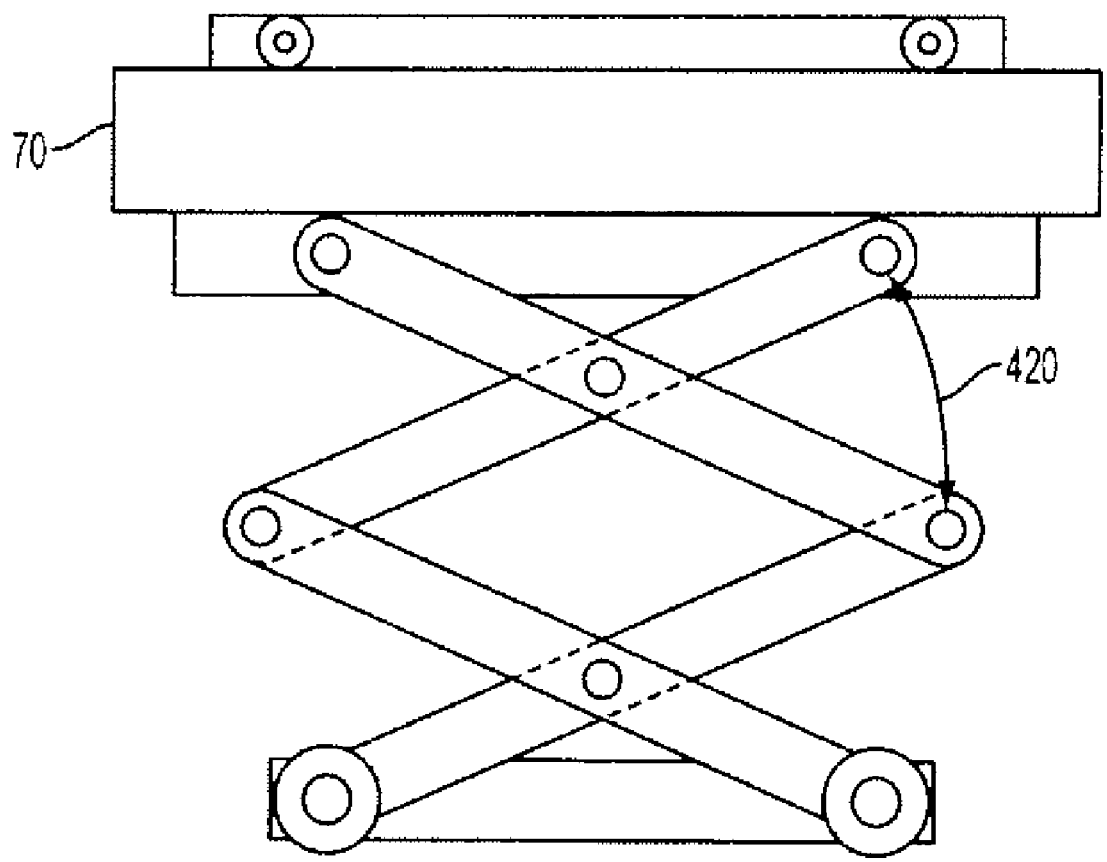
FIG. 5B illustrates an exemplary side view of scissor mechanism 420, in a partially opened position, with patient platform 70 at a top end thereof.

FIG. 5B illustrates an exemplary side view of scissor mechanism 420, in a partially opened position, with patient platform 70 at a top end thereof. The cut away sections of FIGS. 5A and 5B are illustrated as well as a centering pin 490 described above.

Figure 5C:
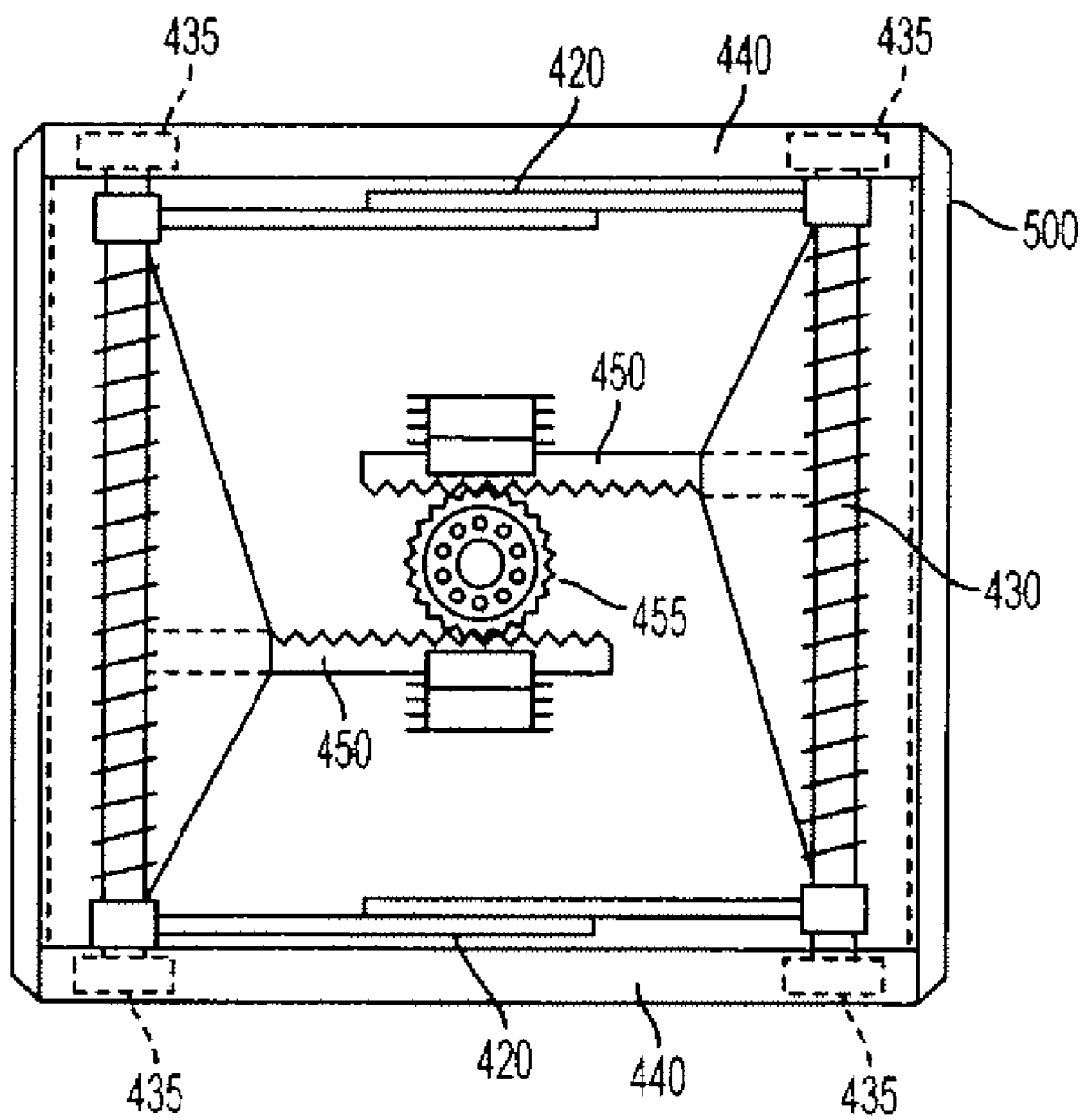
FIG. 5C illustrates an exemplary high level perspective bottom view drawing of patient platform 70, including a scissor mechanism in a closed position.

FIG. 5C illustrates en exemplary bottom view drawing of patient platform 70 in accordance with a principle of the invention, including scissor mechanism 420, beams 430, runners 435, tubes 440, toothed linear members 450 and a tooth gear 455. Scissor mechanism 420 are connected at the ends thereof to beams 430, and beams 430 are connected at their ends to runners 435, which are placed in channels 440. Beams 430 are also connected to a toothed linear member 450. Toothed linear members 450 each mesh with tooth gear 455.

The above has been illustrated in an embodiment in which a pair of independent substantially orthogonal translation mechanisms is provided, however this is not meant to be limiting in any way. In another embodiment a rotation and extension mechanism is provided, enabling translation to achieve a particular positioning along the plane.

Vertical translation mechanism 60 has been described in relation to a scissors mechanism, however this is not meant to be limiting in any way. In particular, in another embodiment a hydraulic mechanism is provided without exceeding the scope of the invention.

Figure 6:
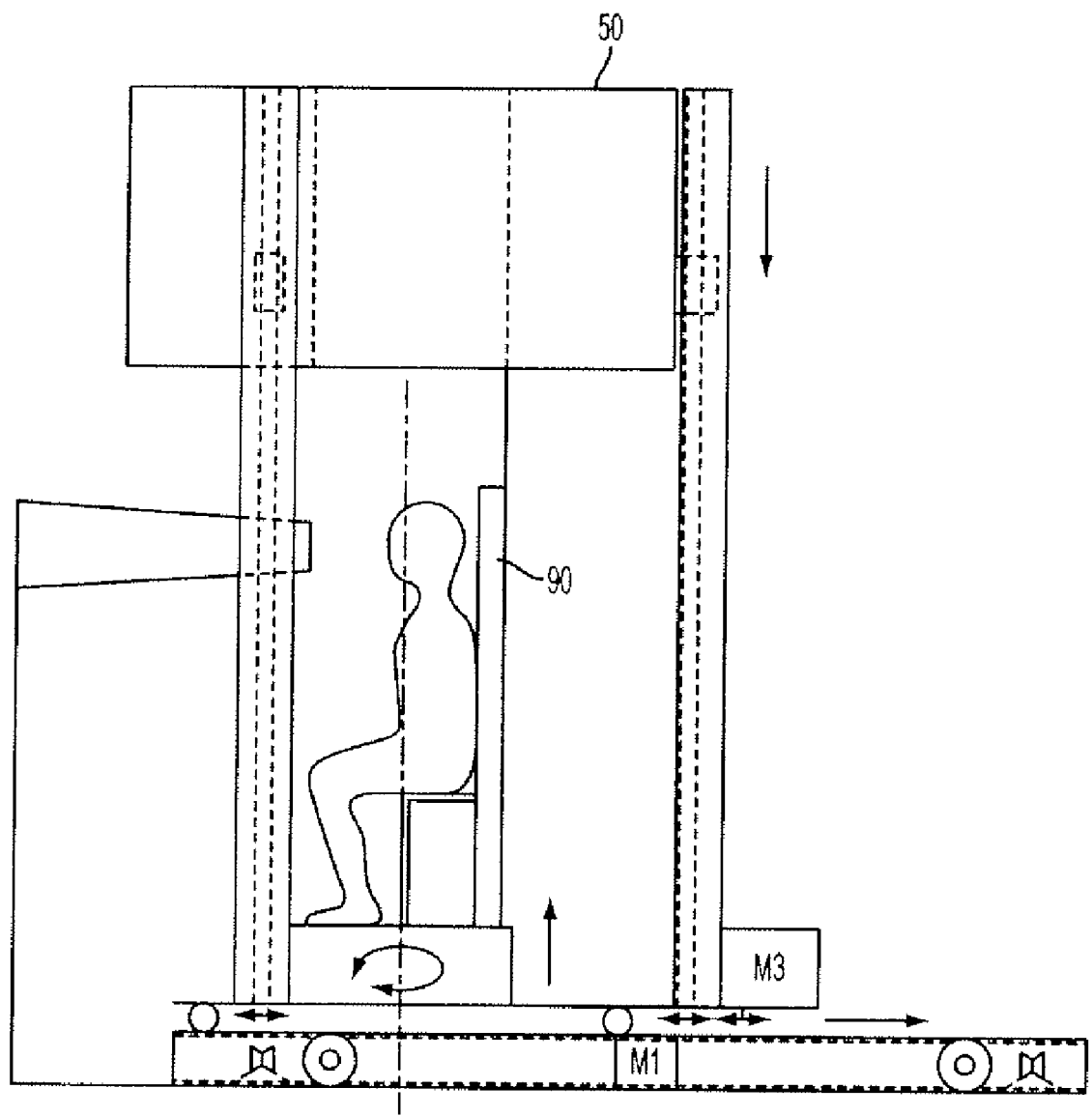
FIG. 6 illustrates an exemplary high level side view of the irradiation treatment apparatus and treatment arrangement of FIG. 1 with a seated patient secured in a generally vertical position against a patient support surface, with the imager in a neutral position.

FIG. 6 illustrates an exemplary high level side view of the irradiation treatment apparatus and treatment arrangement of FIG. 1 with a seated patient secured in a generally vertical position against patient support surface 90, with imager 50 in a neutral position, in which the ultimate beam of irradiation is not occluded.

Figure 7:
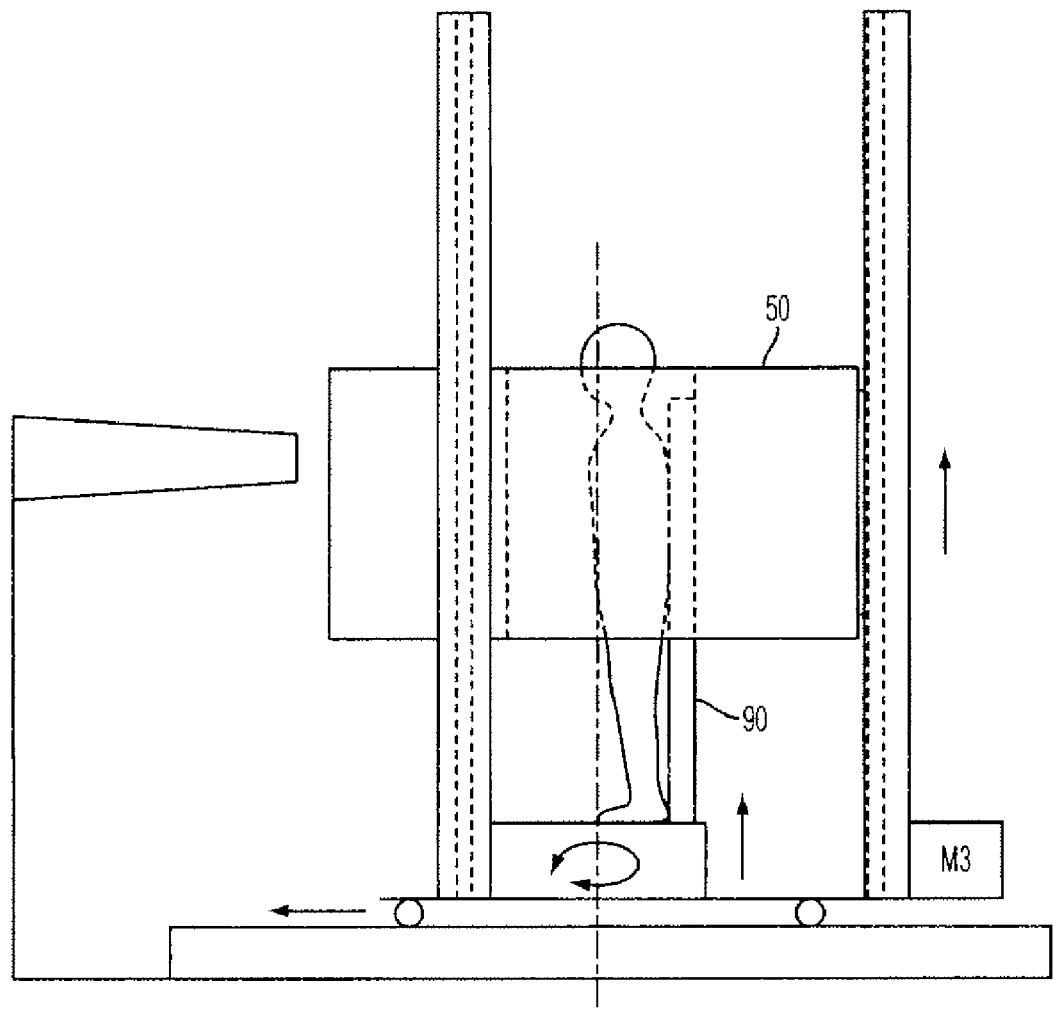
FIG. 7 illustrates an exemplary high level side view of the irradiation treatment apparatus and treatment arrangement of FIG. 1 with a standing patient secured in a generally vertical position against a patient support surface, with the imager in a an imaging position.

FIG. 7 illustrates an exemplary high level side view of the irradiation treatment apparatus and treatment arrangement of FIG. 1 with a standing patient secured in a generally vertical position against patient support surface 90, with imager 50 in an imaging position in accordance with a principle of the invention, in which the ultimate beam of irradiation is occluded.

Figure 8:
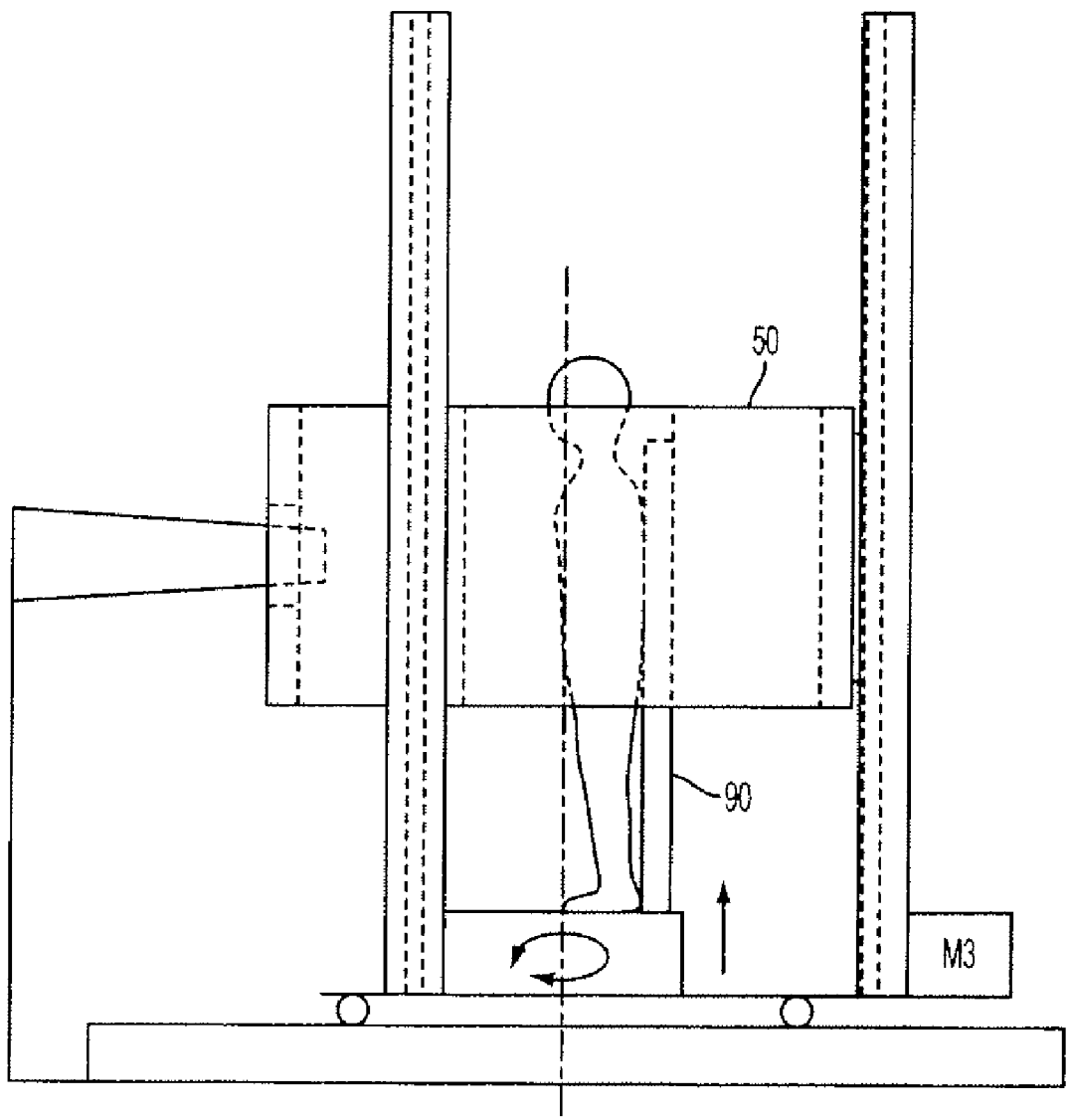
FIG. 8 illustrates an exemplary high level side view of an irradiation treatment apparatus and treatment arrangement in which the imager exhibits a window which when open allows for entry of the fixed beam irradiation source.

FIG. 8 illustrates an exemplary high level side view of an irradiation treatment apparatus and treatment arrangement 600 in which imager 610 exhibits a window 620 which when open allows for entry of the fixed beam irradiation source. Imager 610 need not be translated vertically. In one embodiment imager 601 is in a fixed position. When window 620 is closed, imager 610 performs 360 degrees of imaging suitable for treatment planning and inter-treatment verification. Preferably, when window 620 is open, imager 610 is capable of performing lower resolution imaging sufficient for intra-treatment verification.

Figure 9A:
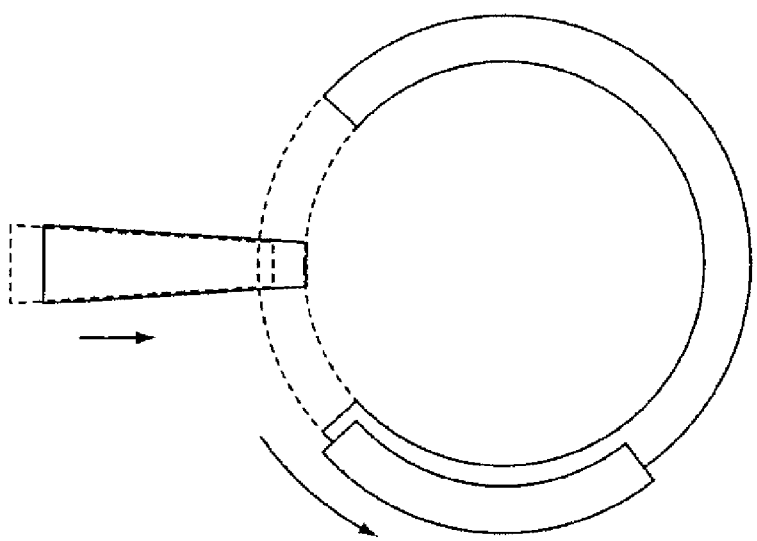
FIG. 9A illustrates an exemplary high level top view of an imager exhibiting a radially shiftable section.
Figure 9B:
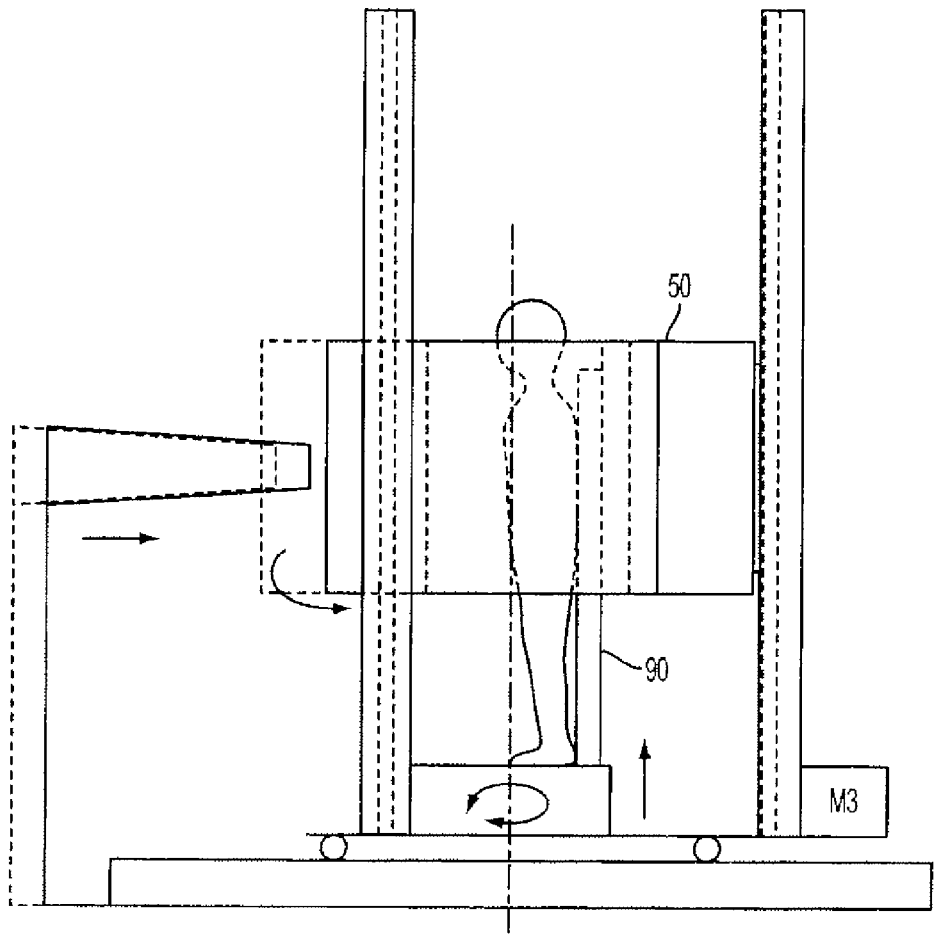
FIG. 9B illustrates an exemplary high level side view of an irradiation treatment apparatus and treatment arrangement in which the imager the imager of FIG. 9A has shifted the radially shiftable section to allow for entry of the fixed beam irradiation source.

FIG. 9A illustrates an exemplary high level top view of an imager 700 exhibiting a radially shiftable section 710. When radially shiftable section 710 is closed, imager 700 performs 360 degrees of imaging suitable for treatment planning and inter-treatment verification. Preferably, when radially shiftable section 710 is open, imager 700 is capable of performing lower resolution imaging sufficient for intra-treatment verification FIG. 9B illustrates an exemplary high level side view of an irradiation treatment apparatus and treatment arrangement in which imager 700 has shifted the radially shiftable section to allow for entry of fixed beam irradiation source 10.

Figure 10:
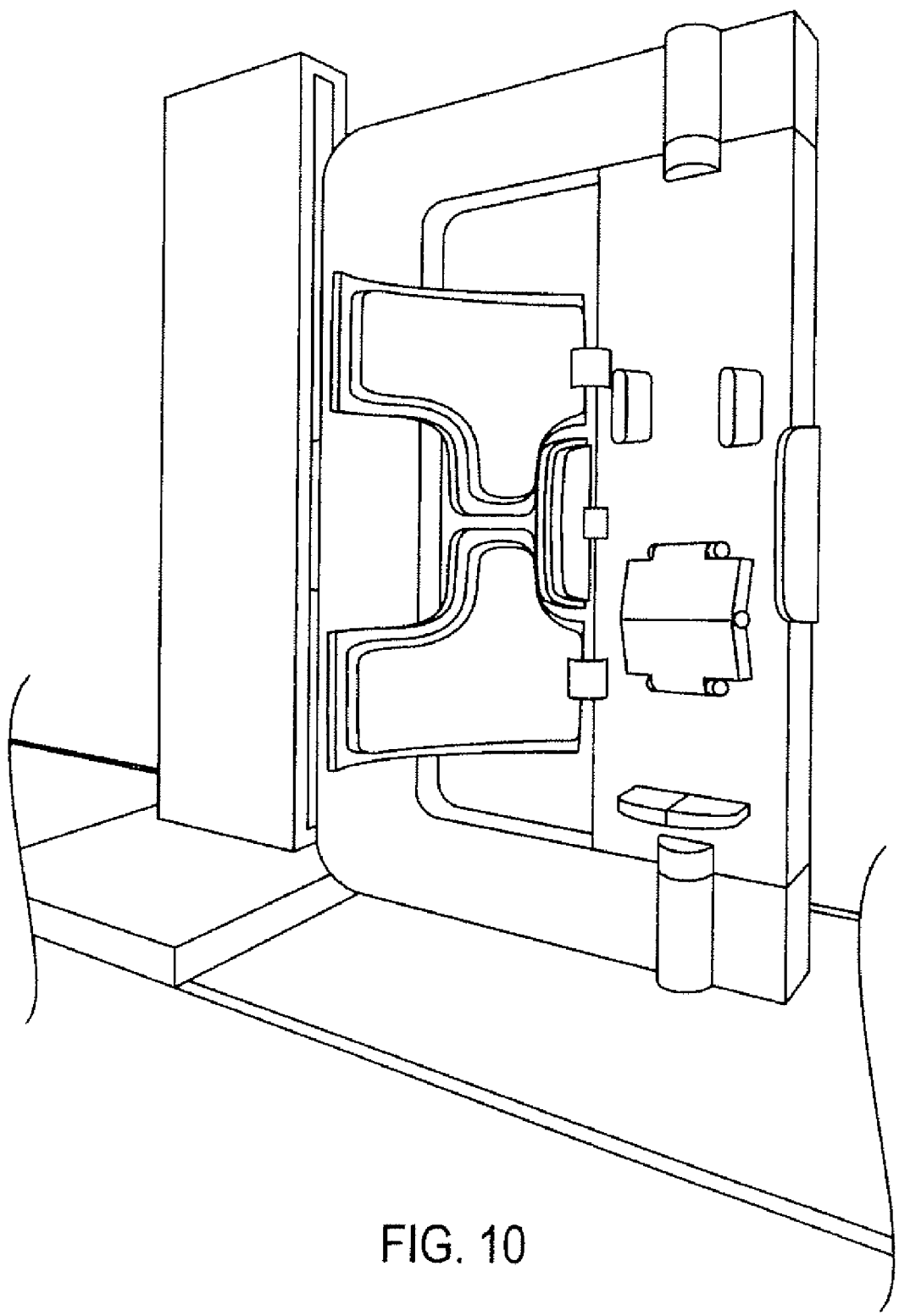
FIG. 10 illustrates an exemplary perspective drawing of an embodiment of a patient support surface.

FIG. 10 illustrates an exemplary perspective drawing of an embodiment of a patient support surface 90, exhibiting a knee support surface 800; movable armpit and/or shoulder supports 810; frontal securing mechanism 820; and foot support 830. Advantageously, knee support surface 800 is foldable into a seat, thereby enabling a sitting or standing presentation with a single patient support surface 90.

Figure 11:
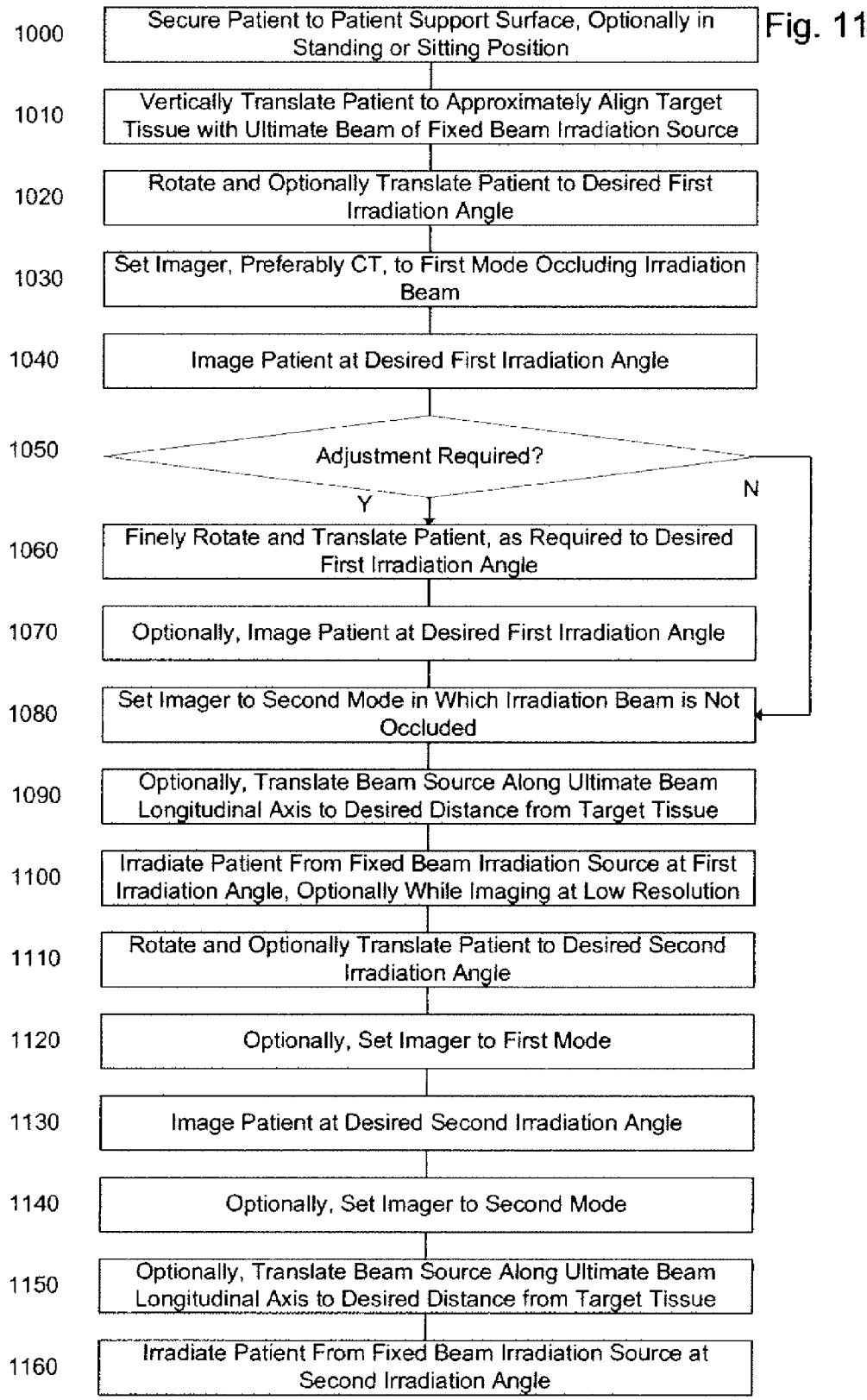
FIG. 11 illustrates an exemplary high level flow chart of an embodiment of a method of irradiation.

FIG. 11 illustrates an exemplary high level flow chart of an embodiment of a method of irradiation. In stage 1000, a patient is secured in a generally vertical position to a patient support surface. Optionally, the patient is secured in one of a standing and a sitting position.

In one or more embodiments, stage 1010, the secured patient is vertically translated to approximately align a target tissue with the ultimate beam of a fixed beam irradiation source. In stage 1020, the secured patient is rotated, and optionally translated along a horizontal plane, to a desired first irradiation angle and presentation. It is to be understood that stage 1010 may be accomplished intermingle with stage 1020, or after stage 1020, without exceeding the scope of the invention.

In stage 1030, the imager, preferably a CT imager, is set to a first mode occluding the treatment irradiation beam. In one embodiment, the imager exhibits a fine resolution. In one embodiment, the imager is translatable between two fixed positions, and in another embodiment the imager is translatable over a range of positions. The imager is thus substantially in-line with and intersects, the ultimate beam from the fixed beam irradiation source.

In another embodiment, as described above in relation to FIG. 8, a window is closed. In yet another embodiment, as described above in relation to FIGS. 9A-9B, a radially shiftable section is closed.

In stage 1040, the patient target tissue is imaged at the first irradiation angle presentation of stages 1010, 1020. In stage 1050, responsive to the imaging of 1050, the target tissue image is viewed to determine if adjustment of the presentation is required. This may be due to changes in the target tissue, or patient registration misalignment.

In the event that adjustment is required, in stage 1060, the secured patient is finely vertically translated, horizontally translated along a horizontal plane and rotated to the desired first irradiation angle and presentation responsive to the imaging of stage 1050. Optionally, in stage 1070 imaging as described above in relation to stage 1040 is again performed to confirm proper presentation, and any further fine adjustment is further performed.

In the event that in stage 1050 no adjustment was required, or after stage 1070, in stage 1080 the imager is set to the second mode in which the fixed beam irradiation source is not occluded. In an embodiment in which the imager is translatable vertically, the imager is translated to a neutral position. In the embodiment, as described above in relation to FIG. 8, the window is opened. In yet another embodiment, as described above in relation to FIGS. 9A-9B a radially shiftable section is shifted to be open, i.e. no longer presenting a closed ring.

In stage 1090, optionally the source of the fixed beam irradiation is translated along the longitudinal axis of the ultimate beam so as to exhibit the desired distance from the target tissue. In another embodiment a nominal position is utilized and the energy level of irradiation is instead modified.

In stage 1100, the patient is irradiated from the fixed beam irradiation source at the first irradiation angle. Optionally, if allowed by the imager in the second mode, such as imager 610 of FIG. 8 and imager 700 of FIGS. 9A, 9B, intra-treatment imaging is accomplished, typically at a lower resolution than the imaging of stage 1040. It is to be understood that preferably the patient position and presentation remains unchanged between the confirming imaging of stages 1040, 1070 and the irradiation of stage 1100.

In the event that multiple irradiation angles and presentations have been prescribed, in stage 1110, the secured patient is rotated about the z-axis as shown in FIG. 1, and optionally translated at least partially along a horizontal plane to a desired second irradiation angle and presentation. Optionally, the secured patient may be further vertically translated as required. In stage 1120, the imager of stage 1030 is set to the first mode. The imager is thus substantially in-line with, and generally occludes, the ultimate beam from the fixed beam irradiation source.

In stage 1130, the patient target tissue is imaged at the second irradiation angle presentation of stage 1110. Adjustment responsive to the imaging, as described above in relation to stages 1050-1070, may be accomplished if required.

In stage 1140 the imager is set to the second mode in which the beam is not occluded, i.e. no longer in-line with the fixed beam irradiation source. In stage 1150, optionally the source of the fixed beam irradiation is translated along the longitudinal axis of the ultimate beam so as to exhibit the desired distance from the target tissue.

In stage 1160, the patient is irradiated from the fixed beam irradiation source at the second irradiation angle. It is to be understood that preferably the patient position and presentation remains substantially unchanged between the confirming imaging of stage 1130 and the irradiation of stage 1160.

The above has been described in an embodiment in which 1 or 2 irradiation angles and presentations are prescribed, however this is not meant to be limiting in any way. In another embodiment, 3 or more irradiation angles and presentations are prescribed by repeating stages 1110-1160 for each additional angle and presentation.

Figure 12:
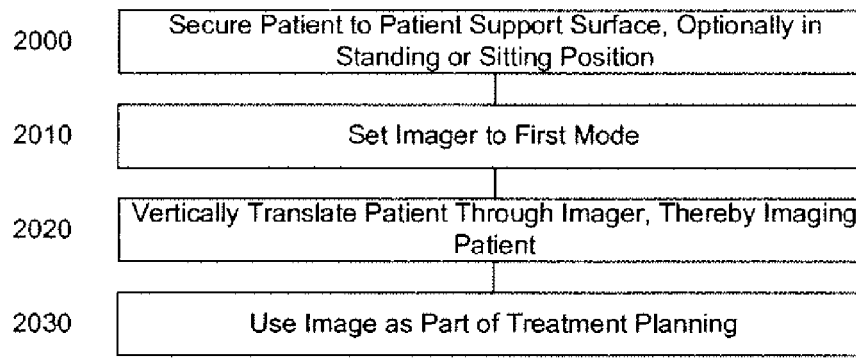
FIG. 12 illustrates an exemplary high level flow chart of an embodiment of a method of treatment planning.

FIG. 12 illustrates an exemplary high level flow chart of an embodiment of a method of treatment planning. In stage 2000, a patient is secured in a generally vertical position to a patient support surface. Optionally, the patient is secured in one of a standing and a sitting position.

In stage 2010, the imager, preferably a CT imager, is set to a first mode. Preferably, the imager exhibits a fine resolution. In one embodiment the imager is translatable between two fixed positions, and in another embodiment the imager is translatable over a range of positions.

In another embodiment, as described above in relation to FIG. 8, a window is closed. In yet another embodiment, as described above in relation to FIGS. 9A-9B a radially shiftable section is closed.

In stage 2020, the secured patient of stage 2000 is translated vertically through the imager of stage 2010 so as to image a slice of the patient. In stage 2030, the image of stage 2020 is used as part of a treatment planning process to determine irradiation angle, power and distance.

Figure 13:
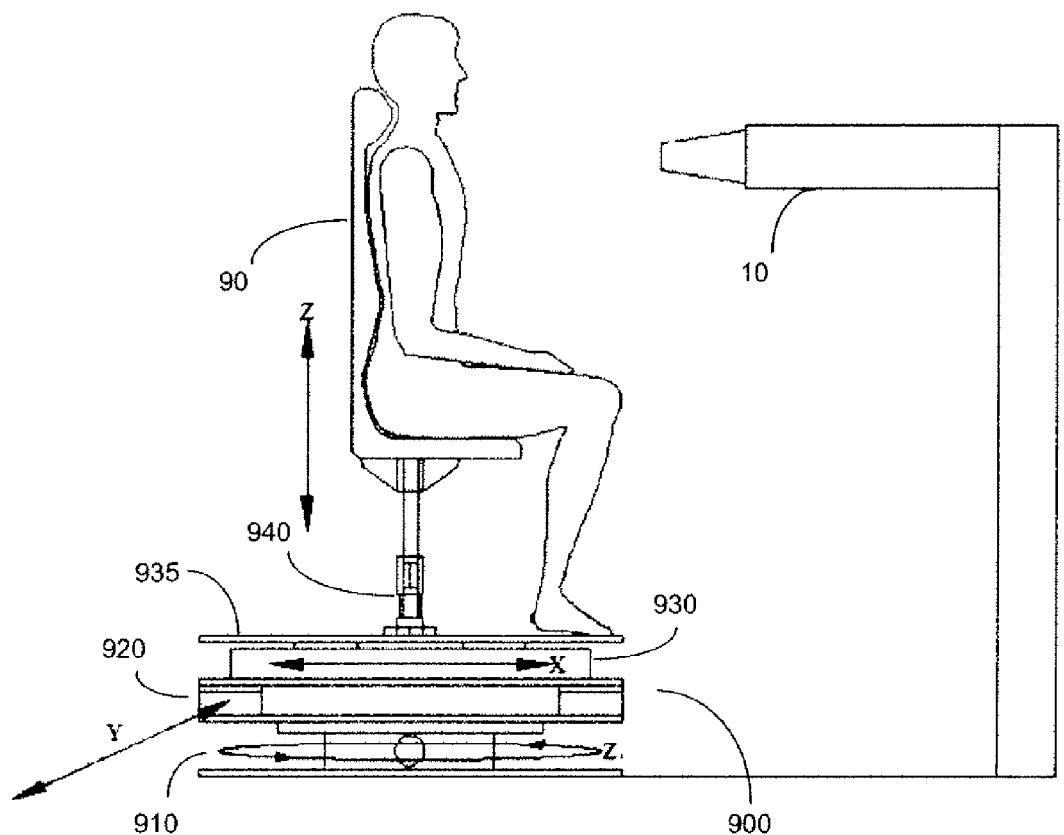
FIG. 13 illustrates an exemplary high level frontal view drawing of a second embodiment of an irradiation treatment apparatus and treatment arrangement.

FIG. 13 illustrates an exemplary high level frontal view drawing of a second embodiment of an irradiation treatment apparatus and treatment arrangement. In some instances, the embodiment of FIG. 13 differs from irradiation treatment apparatus 5 of FIG. 1, primarily in the order of the translation and rotation mechanism. FIG. 13 includes a translation and rotation mechanism 900 constituted of a rotation mechanism 910, a first translation mechanism 920, a second translation mechanism 930 and a platform 935; a patient support surface 90; a vertical translation mechanism 940; and a fixed beam irradiation source 10. Rotation mechanism 910 is in communication with a horizontal base, such as a floor or a platform first translation mechanism 920 is in communication with rotation mechanism 910, and second translation mechanism 930 is in communication with first translation mechanism 920. Platform 935 is in communication with second translation mechanism 930, and via vertical translation mechanism 940 with patient support surface 90. First translation mechanism 920 is arranged to translate along a direction denoted Y, orthogonal to the direction of translation of second translation mechanism 930, whose direction is denoted X. Directions X and Y generally define a plane orthogonal to the axis of rotation of rotation mechanism 910, illustrated as rotation $Z_i$. The direction of motion of vertical translation mechanism 940 is denoted Z.

Advantageously, the arrangement of FIG. 13 allows for setting the isocenter of a target tissue to be aligned with the output beam from fixed beam irradiation source 10, and to be rotated about an axis Z generally along the isocenter of the target tissue.

The above has been described in an embodiment in which patient support surface 90 is generally vertical, however this is not meant to be limiting in any way. Patient support surface 90 may in one embodiment enable a tilt of up to 15° from vertical without exceeding the scope of the invention. In another embodiment, patient support surface 90 is generally vertical; however a separate tilting head support is provided allowing for tilting of the head while maintaining the patient body in a generally upright position.

Thus, the present embodiments enable an irradiation treatment apparatus comprising a patient securing means arranged to secure a patient in generally vertical position to a patient support surface. The patient support surface is connected at one end to a rotation and translation platform, arranged to rotate the patient support surface about a generally vertical axis thereof, and to translate the patient support surface along a plane perpendicular to the axis of rotation. The patient support surface is further translatable vertically, generally along the axis of rotation. An imager, preferably a computerized tomography imager exhibiting fine resolution and a large scan width is provided and arranged to exhibit two modes: a first mode in which the beam of irradiation is occluded and a second mode in which the beam if irradiation is not occluded.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

We claim:

1. An irradiation treatment apparatus comprising:
   a patient support surface;
   a rotation mechanism;
   a patient securing mechanism arranged to secure a patient in a fixed relation to said patient support surface;
   a platform in communication with said patient support surface and said rotation mechanism and arranged to rotate said patient support surface about a generally vertical axis;
   an imager exhibiting a window and a first mode in which said imager occludes radiation from a fixed beam irradiation source when said window is closed and a second mode in which said imager enables irradiation from the fixed beam irradiation source when said window is open;
   a vertical translation mechanism in communication with said patient support surface and arranged to translate said patient support surface along said generally vertical axis from a loading position to an irradiation position; and
   a control unit in communication with said imager, said control unit operative to:
   set said imager to said first mode;
   translate said patient support system vertically through said imager via said vertical translation mechanism, and operate said imager to thereby image a section of the patient.

2. An irradiation treatment apparatus according to claim 1, wherein said imager in said second mode is operative to perform intra-treatment imaging.

3. An irradiation treatment apparatus according claim 1, wherein said imager is arranged to perform computerized tomography.

4. An irradiation treatment apparatus according to claim 1, wherein said vertical translation mechanism is coupled to said platform thereby in said communication with said patient support surface.

5. An irradiation treatment apparatus according to claim 1, further comprising a horizontal translation mechanism coupled to said platform, said horizontal translation mechanism operative to translate said patient support surface along a pair of orthogonal axes perpendicular to said generally vertical axis.

6. An irradiation treatment apparatus according to claim 1, wherein said irradiation position aligns a target tissue of the secured patient with a beam of radiation ultimately exiting a fixed beam irradiation source.

7. An irradiation treatment apparatus according to claim 1, wherein said imaging of said section at least partially provides for treatment planning.

8. An irradiation treatment apparatus according to claim 1, further comprising a fixed beam radiation source.

9. An irradiation treatment apparatus according to claim 1, wherein said patient support surface is generally vertical.

10. An irradiation treatment apparatus according to claim 9, wherein said generally vertical patient support surface exhibits a chair mode in which the spine of the patient is generally secured vertically by said generally vertical patient support surface.

11. A method comprising:
   securing a patient to a patient support surface;
   vertically translating the secured patient so as to approximately align a target tissue of the secured patient with an treatment irradiation beam ultimately exiting a fixed beam irradiation source;
   rotating the secured patient about a generally vertical axis so as to approximately present the target tissue to the treatment irradiation beam ultimately exiting the fixed beam irradiation source at a first desired angle;
   providing an imager exhibiting a window and a first mode in which said provided imager occludes radiation from a fixed beam irradiation source when said window is closed and a second mode in which said provided imager enables irradiation from the fixed beam irradiation source when said window is open;
   setting said provided imager to said first mode;
   translating said patient support surface vertically through said provided imager via said vertical translation mechanism thereby imaging, via said imager in said first mode, said target tissue aligned with the treatment irradiation beam ultimately exiting the fixed beam irradiation source;
   setting said imager to said second mode; and
   irradiating the target tissue from said fixed beam irradiation source at said first desired angle.

12. A method according to claim 11, further comprising subsequent to said imaging said target tissue, at least one of:
   finely vertically translating, responsive to said imaging, the secured patient so as to align the target tissue of the secured patient with the treatment irradiation beam ultimately exiting a fixed beam irradiation source at said first desired angle; and
   finely rotating the secured patient about the generally vertical axis, responsive to said imaging, so as to present the target tissue to the treatment irradiation beam ultimately exiting the fixed beam irradiation source at said first desired angle.

13. A method according to claim 11, further comprising prior to said irradiating, translating a source of irradiation along a longitudinal axis of the ultimate radiation beam, so as to achieve a desired distance between the fixed beam irradiation source and said target tissue.

14. A method according to claim 11, wherein the imager is arranged to perform computerized tomography.

15. A method according claim 11, wherein said securing the patient to a patient support surface is in one of a standing and a sitting position.

16. A method according to claim 11, further comprising subsequent to said irradiating at said first desired angle:
   rotating about a generally vertical axis, and translating about a plane orthogonal to said generally vertical axis, the secured patient so as to approximately present the target tissue to the treatment irradiation beam ultimately exiting the fixed beam irradiation source at a second desired angle;
   setting the imager to said first mode;
   imaging, via said imager, said target tissue aligned with the treatment irradiation beam ultimately exiting the fixed beam irradiation source;
   setting said imager to said second mode; and
   irradiating the target tissue from said fixed beam irradiation source at said second desired angle.

\* \* \* \* \*